(12) United States Patent
Voegele

(10) Patent No.: US 6,425,903 B1
(45) Date of Patent: Jul. 30, 2002

(54) IMPLANTABLE SURGICAL MARKER

(76) Inventor: James W. Voegele, 11486 Kemperknoll Rd., Cincinnati, OH (US) 45249

( * ) Notice: Subject to any disclaimer, the term of this patent is extended or adjusted under 35 U.S.C. 154(b) by 0 days.

(21) Appl. No.: 09/567,211

(22) Filed: May 9, 2000

(51) Int. Cl.⁷ .............................................. A61B 17/08
(52) U.S. Cl. ..................... 606/151; 606/219; 606/220; 606/157; 606/116; 411/472
(58) Field of Search ................... 606/219, 220, 606/221, 151, 157, 213, 215, 139, 143, 155, 72, 75, 116; 600/562; 128/899; 411/457, 460, 461, 463, 471, 470, 472, 475, 481, 920

(56) References Cited

U.S. PATENT DOCUMENTS

| | | | | |
|---|---|---|---|---|
| 1,311,903 A | * | 8/1919 | Leschander ................. | 411/472 |
| 2,034,080 A | * | 3/1936 | Bitzenburger ............... | 411/472 |
| 2,111,404 A | | 3/1938 | Pankonin ...................... | 85/49 |
| 2,347,961 A | | 5/1944 | Olsen .......................... | 72/118 |
| 2,549,731 A | | 4/1951 | Wattley | |
| 2,624,085 A | * | 1/1953 | Feiner ......................... | 411/471 |
| 3,150,379 A | | 9/1964 | Brown | |
| 3,203,220 A | | 8/1965 | Kaepernik ................... | 72/410 |
| 3,273,562 A | | 9/1966 | Brown ........................ | 128/337 |
| 3,583,663 A | | 6/1971 | Snow, Jr. et al. ............. | 248/71 |
| 4,080,959 A | | 3/1978 | Leveen ....................... | 128/2 H |
| 4,114,859 A | | 9/1978 | Stenson ...................... | 256/48 |
| 4,399,810 A | | 8/1983 | Samuels et al. ............. | 128/337 |
| 4,407,283 A | | 10/1983 | Reynolds .................... | 128/334 |
| 4,505,273 A | | 3/1985 | Braun et al. ................. | 128/335 |
| 4,586,503 A | | 5/1986 | Kirsch et al. ................ | 128/334 |
| 4,607,638 A | | 8/1986 | Crainich ..................... | 128/335 |
| 4,649,151 A | | 3/1987 | Dougherty et al. .......... | 514/410 |
| 4,697,045 A | * | 9/1987 | Beatty ........................ | 411/471 |
| 4,733,664 A | | 3/1988 | Kirsch et al. ................ | 128/334 |
| 4,762,260 A | | 8/1988 | Richards et al. ............. | 227/19 |
| 4,787,387 A | | 11/1988 | Burbank, III et al ........ | 128/334 |
| 4,874,122 A | | 10/1989 | Froelich et al. .............. | 227/19 |
| 4,983,176 A | | 1/1991 | Cushman et al. ............ | 606/151 |
| 5,147,307 A | | 9/1992 | Gluck ......................... | 604/116 |
| 5,192,270 A | | 3/1993 | Carswell, Jr. ................ | 604/116 |
| 5,209,754 A | | 5/1993 | Ahluwalia ................... | 606/199 |
| 5,221,269 A | | 6/1993 | Miller et al. ................. | 604/281 |

(List continued on next page.)

FOREIGN PATENT DOCUMENTS

WO     WO9608208 A1    3/1996

OTHER PUBLICATIONS

Sandra S. Kramer, M. D. et al. "A Permanent Radiopaque Marker Technique for the Study of Pharyngeal Swallowing in Dogs" Dysphagia 1:163–167 (1987).

*Primary Examiner*—Amy B. Vanatta

(57) ABSTRACT

An implantable marker for implantation in tissue of a surgical patient is disclosed. The marker has a base and an elevated bridge. A pair of legs descend from first and second transitions of the bridge. Each leg has a distal tip, a generally straight leg arm adjacent the tip, a camming marker surface between the transitions of the base and the straight leg arm, and a camming marker surface notch. The camming marker surfaces extend outwardly from the straight leg arms of the legs. In its pre-formed configuration, the first and second straight leg arms of the legs of the marker are generally parallel to each other. In its open form configuration, the first and second straight leg arms initially converge towards each other, then diverge into an open form generally taking the shape of the letter "W". The marker is particularly adapted for fixation in tissue to mark the site of a lesion or other abnormal tissue which may be removed during a biopsy procedure, for example a breast biopsy procedure. Advantageously, the camming marker surfaces of the legs of the marker and the camming marker surface notches facilitate the ability to form the marker upon pushing the marker distally into the tissue, thus insuring deep penetration and anchoring of the marker securely in the tissue regardless of tissue density.

9 Claims, 3 Drawing Sheets

U.S. PATENT DOCUMENTS

| | | |
|---|---|---|
| 5,222,975 A | 6/1993 | Crainich .................... 606/219 |
| 5,240,011 A | 8/1993 | Assa ......................... 128/751 |
| 5,246,156 A | 9/1993 | Rothfuss et al. ............ 227/176 |
| 5,366,479 A | 11/1994 | McGarry et al. ........... 606/219 |
| 5,695,524 A * | 12/1997 | Kelley et al. ............... 606/219 |
| 5,941,890 A | 8/1999 | Voegele et al. ............. 606/151 |
| 6,173,715 B1 * | 1/2001 | Sinanan et al. ............. 128/898 |
| 6,181,960 B1 * | 1/2001 | Jensen et al. ................ 606/116 |
| 6,228,055 B1 * | 5/2001 | Foerster et al. ............. 606/116 |
| 6,325,805 B1 * | 12/2001 | Ogilvie et al. ................ 606/72 |
| 6,350,244 B1 * | 2/2002 | Fisher ........................ 606/116 |
| 6,352,541 B1 * | 3/2002 | Kienzle et al. ............. 606/143 |

\* cited by examiner

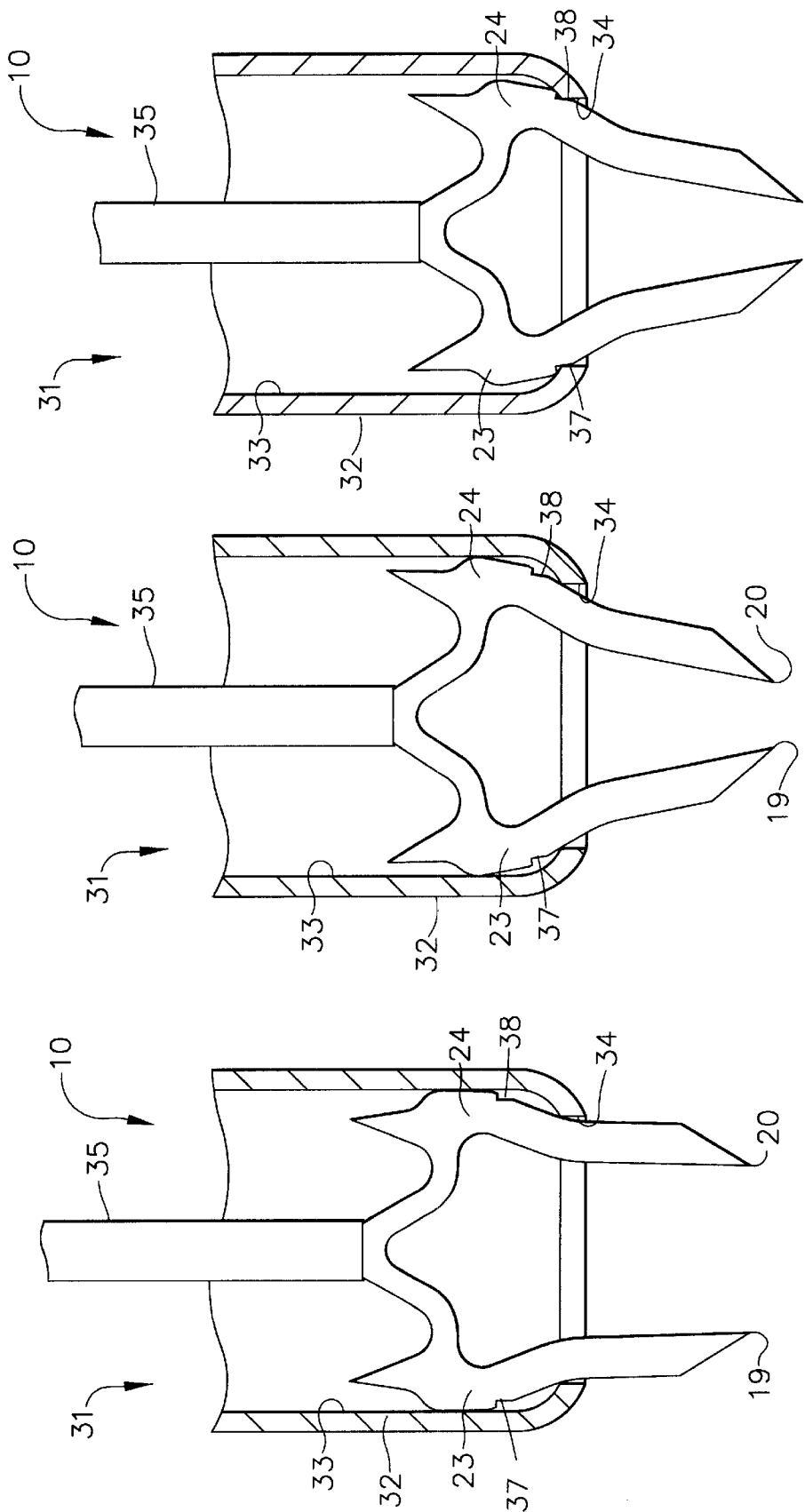

IMPLANTABLE SURGICAL MARKER

BACKGROUND OF THE INVENTION

This invention relates to a marker for implantation in tissue of a surgical patent. More specifically, it relates to an implantable marker for defining particular locations in human tissue, particularly in a human breast.

One in nine American women will develop breast cancer in their lifetime. It is the leading cause of cancer deaths in women 40–55 years of age and the second leading cause of cancer deaths in women overall. Breast cancer will be diagnosed in approximately one in eight women in their lifetime, and one in 30 will die of this disease. Breast cancer does occur in males but is much less common. Biopsy requests stem from a screening process generally performed via a physical examination (palpable) and/or mammogram (non-palpable). A biopsy is indicated if suspicious tissue is detected. Five out of six biopsies performed return benign indications.

It is desirable and often necessary to perform procedures for detecting, sampling, and testing lesions and other abnormalities in the tissue of humans and other animals, particularly in the diagnosis and treatment of patients with cancerous tumors, pre-malignant condition and other diseases or disorders. Typically, in the case of cancer, when a physician establishes by means of known procedures (i.e. palpation, x-ray, MRI, or ultrasound imaging) that suspicious circumstances exist, a biopsy is performed to determine whether the cells are cancerous. Biopsy may be an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In FNA biopsy, very small needles are used to obtain individual cells or clusters of cells for cytologic examination. The cells may be prepared such as in a Papanicolaou (Pap) smear. In core biopsy, as the term suggests, a core or fragment of tissue is obtained for histologic examination, which may be done via a frozen section or paraffin section. The chief difference between FNA and core biopsy is the size of the tissue sample taken. An imaging system having spectroscopic capabilities, such as the stereotactic guidance system described in U.S. Pat. No. 5,240,011 is employed to guide the extraction instrument to the lesion.

Depending on the procedure being performed, the sample may result in the suspicious lesion being partially or completely removed. Visibility of the lesion by the imaging system may be hampered because of the distortion created by the extraction process itself as well as associated bleeding in the surrounding tissues. Although the lesion is removed and all fluids are continuously aspirated from the extraction site, it is likely that the process will "cloud" the lesion, thus impairing exact recognition of its margins. This makes it difficult to ensure that the entire lesion will be removed.

Often, the lesion is merely a calcification derived from dead abnormal tissue, which may be cancerous or pre-cancerous, and it is desirable to remove only a sample of the lesion, rather than the entire lesion, to evaluate it. This is because such a lesion actually serves to mark or define the location of adjacent abnormal tissue, so the physician does not wish to remove the entire lesion and thereby lose a critical means for later relocating the affected tissue. One of the benefits to the patient from core biopsy is that the mass of the tissue taken is small. However, oftentimes, either inadvertently or because the lesion is too small, the entire lesion is removed for evaluation, even though it is desirable to remove only a portion. Then, if subsequent analysis indicates the tissue to be malignant (malignant tissue requires removal, days or weeks later, of tissue around the immediate site of the original biopsy), it is difficult for the physician to determine the precise location of the lesion, in order to perform necessary additional procedures on adjacent potentially cancerous tissue. Additionally, even if the lesion is found to be benign, there will be no evidence of its location during future examinations, to mark the location of the previously removed calcification so that the affected tissue may be carefully monitored for future reoccurrence.

Thus, it would be of considerable benefit to be able to permanently mark the location or margins of such a lesion prior to or immediately after removing the sample. Marking prior to removal would help to ensure that the entire lesion is excised, if desired. Alternatively, if the lesion were inadvertently removed in its entirety, marking the biopsy site immediately after the procedure would enable re-establishment of its location for future identification.

A number of procedures and devices for marking and locating particular tissue locations are known in the prior art. For example, location wire guides, such as that described in U.S. Pat. No. 5,221,269 to Miller et al, are well known for locating lesions, particularly in the breast. The device described by Miller comprises a tubular introducer needle and an attached wire guide, which has at its distal end a helical coil configuration for locking into position about the targeted lesion. The needle is introduced onto the breast and guided to the lesion site using an imaging system of a known type, for example, x-ray, ultrasound or magnetic resonance imaging (MRI), at which time the helical coil at the distal end is deployed about the lesion. Then, the needle may be removed from the wire guide, which remains in a locked position distally about the lesion for guiding a surgeon down the wire to the lesion site during subsequent surgery. While such a location system is effective, it is obviously intended and designed to be only temporary, and is removed once the surgery or other procedure has been completed.

Other devices are known for marking external regions of a patient's skin. For example, U.S. Pat. No. 5,192,270 to Carswell, Jr. discloses a syringe which dispenses a colorant to give a visual indication on the surface of the point at which an injection has or will be given. Similarly, U.S. Pat. No. 5,147,307 to Gluck discloses a device which has patterning elements for impressing a temporary mark in a patients skin, for guiding the location of an injection or the like. It is also known to tape or otherwise adhere a small metallic marker, e.g. a 3 millimeter diameter lead sphere, on the skin of a human breast in order to delineate the location of skin calcifications (see Homer et al, The Geographic Cluster of Microcalcifications of the Breast, Surgery, Gynecology, & Obstetrics, December 1985). Obviously, however, none of these approaches are useful for marking and delineating internal tissue abnormalities, such as lesions or tumors.

Still another approach for marking potential lesions and tumors of the breast is described in U.S. Pat. No. 4,080,959. In the described procedure, the skin of the portion of the body to be evaluated, such as the breasts, is coated with a heat sensitive color-responsive chemical, after which that portion of the body is heated with penetrating radiation such as diathermy. Then, the coated body portion is scanned for color changes which would indicate hot spots beneath the skin surface. These so-called hot spots may represent a tumor or lesion, which does not dissipate heat as rapidly because of its relatively poor blood circulation (about $\frac{1}{20}$ of the blood flow through normal body tissue). This method, of course, functions as a temporary diagnostic tool, rather than in a permanent means for delineating the location of a tumor or lesion.

A method of identifying and treating abnormal neoplastic tissue or pathogens within the body is described in U.S. Pat. No. 4,649,151 to Doughety et al. In this method, a tumor-selective photosensitizing drug is introduced into a patient's body, where it is cleared from normal tissue faster than it is cleared from abnormal tissue. After the drug clears normal tissue but before it has cleared abnormal neoplastic tissue, the abnormal neoplastic tissue may be located by the luminescence of the drug within the abnormal tissue. The fluorescence may be observed with low intensity light, some of which is within the drug's absorbency spectrum. Once detected, the tissue may be destroyed by further application of higher intensity light having a frequency within the absorbency spectrum of the drug. Of course, this method also is only a temporary means for marking the abnormal tissue. Additionally, once the abnormal tissue has been destroyed during treatment, the marker is destroyed as well.

It is also known to employ biocompatible dyes or stains to mark breast lesions. First, a syringe containing the colorant is guided to a detected lesion, using an imaging system. Later, during the extraction procedure, the surgeon harvests a tissue sample from the stained tissue. However, while such staining techniques can be effective, it is difficult to precisely localize the stain. Also, the stains are difficult to detect flouoroscopically and may not always be permanent.

Additionally, it is known to implant markers directly into a patient's body using invasive surgical techniques. For example, during a coronary artery bypass graft (CABG), which of course constitutes open-heart surgery, it is common practice to surgically apply one or more metallic rings to the aorta at the site of the graft. This enables a practitioner to later return to the site of the graft by identifying the rings, for evaluative purposes. It is also common practice to mark a surgical site with staples, vascular clips, and the like, for the purpose of future evaluation of the site.

A technique has been described for the study of pharyngeal swallowing in dogs, which involves permanently implanting steel marker beads in the submucosa of the pharynx (S. S. Kramer et al, A Permanent Radiopaque Marker Technique for the Study of Pharyngeal Swallowing of Dogs, Dysphagia, Vol. 1, pp.163–167, 1987). The article posits that the radiographic study of these marker beads during swallowing on many occasions over a substantial period of time provides a better understanding of the pharyngeal phase of deglutition on humans. In the described technique, the beads were deposited using a metallic needle cannula having an internal diameter slightly smaller than the beads to be implanted. When suction was applied to the cannula, the bead sat firmly on the tip. Once the ball-tipped cannula was inserted through tissue, the suction was broken, thereby releasing the bead, and the cannula is withdrawn.

Of course, this technique was not adapted or intended to mark specific tissue sites, but rather to mark an entire region or structure of the body in order to evaluate anatomical movements (i.e. swallowing motions). It also was not intended for use in humans.

Accordingly, what is needed is a method and device for non-surgically implanting potentially permanent markers at the site of a lesion or other abnormal tissue, for the purpose of defining the margins of a lesion before it is removed and/or to establish its location after it has been removed. The markers should be easy to deploy and easily detected using state of the art imaging techniques.

A method of implanting markers directly into a patient's body using minimally invasive surgical techniques is described in International Patent No. WO 9608208A1 to Foerster et al. In this method, a clipping device is introduced to the lesion site by a tubular cannula. Once the clip is at the lesion site, an actuating means at the proximal end outside the patient deploys the clip into the tissue. This marking means can be used long term and can be imaged by most imaging techniques. However, because of its small size, current ultrasound imaging systems are unable to detect it within the tissue.

Another method of implanting a marker is described in U.S. Pat. No. 5,902,310 to Foerster et al. The marker described in this method utilizes a central tang that is tensily loaded to cause a squarely supported, end contact bridge on the marker to bend resulting in the goal post arms to swing inward in an arcuate fashion to pinch tissue. The tensile load on the tang is increased until it breaks at a predetermined location leaving the marker attached to the tissue site. Unfortunately, this method requires the marker to be pulled away from tissue when the marker is formed, consequently, limiting marker penetration and the amount of tissue grasped.

A surgical clip for permanently joining opposed tissue for an anastomosis procedure is described in U.S. Pat. No. 4,733,664 to Kirsh et al. This is accomplished using an applier, also disclosed, to pull on a frangible central tang to close a pair of spaced arcuate arms extending generally parallel in one direction from opposite ends of the plastically deformable bridge. The arms are brought around opposed tissue. A predetermined force is applied to create a tensile break of the neck in the tang. Specific angles of clip shoulder and applier are given. The applier jaw faces are in the range of 120° to 180° with respect to one another, specifically 150° Unfortunately, the method of forming this clip suffers a fate similar to the method described in the preceding paragraph.

U.S. Pat. No. 5,941,890 to Voegele et al describes an implantable marker for implantation into a surgical patient. The marker is described as comprising a base, and first and second legs extending from the base. The base of the marker includes an elevated bridge. The first and second legs are generally straight and generally parallel to each other in the marker's pre-formed condition. Each leg includes a camming surface on its exterior wall. The appearance of the marker, in its pre-formed condition, is similar to the letter "U".

To administer the marker described in the '890 patent, an applier is used. The applier includes a push rod and tube with a camming wall surface at its distal end. The push rod functions to contact the elevated bridge of the marker and push the marker from the applier into the targeted tissue. As the marker is pushed, the camming surface on each leg of the marker is cammed against the camming wall surface of the applier. This interaction causes the distal tips of the marker legs to converge towards each other as the elevated bridge deforms, causing the targeted tissue to become entrapped between the legs. The marker is fully formed essentially when the distal tips of the legs touch, the formed marker now generally diamond shaped. As the push rod continues to apply force to the elevated bridge, the marker exits the distal end of the applier. The benefits of this marker are described as its ability to be pushed into tissue for deeper penetration and an ability to "grasp" a greater amount of tissue in contrast to conventional markers.

The deeper penetration is indeed a great attribute, however, the depth of penetration is largely determined by the composition and density of the tissue to which the marker is applied. The breast, for example, is made up of a wide range of densities of tissue, from very soft, fatty tissue to very firm and dense muscular tissue. The marker described may indeed penetrate and grasp very soft, fatty tissue, however the structure of the tissue may be such that the marker would easily tear away from the tissue, leaving the marker to move and migrate within the breast, obviously an undesirable condition. Similarly if the tissue involved is extremely dense, i.e. muscular, the marker may meet resistance to forming into its final "diamond" shape. As a result, the marker may not be securely attached to the tissue and again may become dislodged.

Furthermore, the marker described, in its final diamond formation, is relatively small and compact in size. This attribute may make the marker more difficult to identify on x-ray images or images from other known imaging modalities previously described.

Accordingly, what is needed is a surgical marker for implantation at the sites of a lesion or other abnormal tissue, for the purpose of defining the margins of a lesion before it is removed or to establish its location after it has been removed. The marker should be easy to deploy and more easily detected using state of the art imaging techniques. Additionally, the marker must be capable of being securely anchored into a wide range of tissue densities without risk of becoming dislodged.

SUMMARY OF THE INVENTION

The invention is an implantable marker for implantation in tissue of a surgical patient. The marker comprises a base, and first and second legs.

The base of the marker includes an elevated bridge. The bridge has a top and a pair of top arcuate surfaces separated by the top. The bridge is bounded by first and second transitions.

The first leg descends from the first transition of the base. The first leg includes the following: a) a first distal tip remote from the first transition, b) a generally straight first leg arm adjacent the first distal tip, and c) a first camming marker surface between the first transition of the base and the first straight leg arm. The first camming marker surface extends outwardly from the first straight leg arm.

The second leg of the marker descends from the second transition of the base. The second leg includes the following: a) a second distal tip remote from the first transition, b) a generally straight second leg arm adjacent the second distal tip, and c) a second camming marker surface between the second transition of the base and the second straight leg arm. The second camming marker surface extends outwardly from the straight second leg arm. A first camming marker surface notch is located on the first camming marker surface. A second camming marker surface notch is located on the second camming marker surface.

The first and second straight leg arms are generally parallel to each other when the marker is in a pre-formed configuration. The first and second straight leg arms initially converge towards each other from a spaced-apart position adjacent the first and second transitions and then diverge into an open form configuration so that the distal tips of the legs are separated from each other.

Significantly, the first and second camming marker surface notches on the camming marker surfaces of the legs of the marker of this invention facilitate the deployment of the marker in a manner in which the marker can be pushed into the tissue during deployment for deep tissue penetration regardless of the particular tissue characteristics. This is so because as the legs initially converge and then diverge, the marker is securely anchored in the tissue notwithstanding whether the tissue is soft and fatty or dense and muscular. In addition, and in contrast to the prior art markers, the marker of this invention is less likely to unintentionally dislodge because of its enhqanced anchoring ability in its open form configuration. Furthermore, the final open form configuration of the marker also contributes to its ability to be more easily identified on x-ray images or images from other known imaging modalities.

The marker of this invention is especially adapted for implantation at the site of a lesion or other abnormal tissue particularly during a biopsy procedure to define the margins of a lesion before it is biopsied or to establish its location at some later time after the biopsy sample has been removed.

BRIEF DESCRIPTION OF THE DRAWINGS

FIG. 4 is a fragmentary distal end sectional view illustrating the plan view of the marker of FIG. 1 in its loaded position within the shaft of an applier.

FIGS. 5–9 are fragmentary distal end sectional views illustrating sequentially the formation of the loaded marker depicted in FIG. 4.

DETAILED DESCRIPTION OF THE PREFERRED EMBODIMENT

Figure 3:
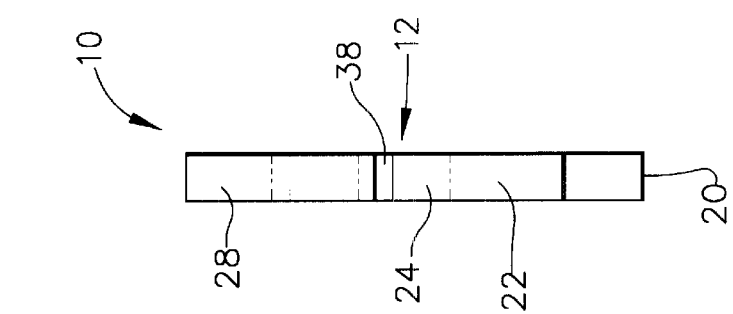
FIG. 3 is a side elevational view of the marker of FIG. 1.
Figure 2:
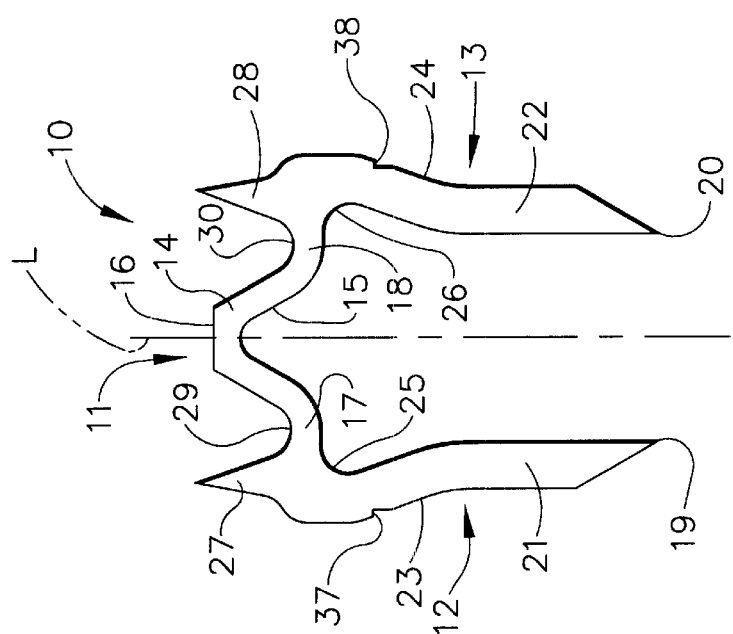
FIG. 2 is a front elevational view of the marker of FIG. 1.
Figure 1:
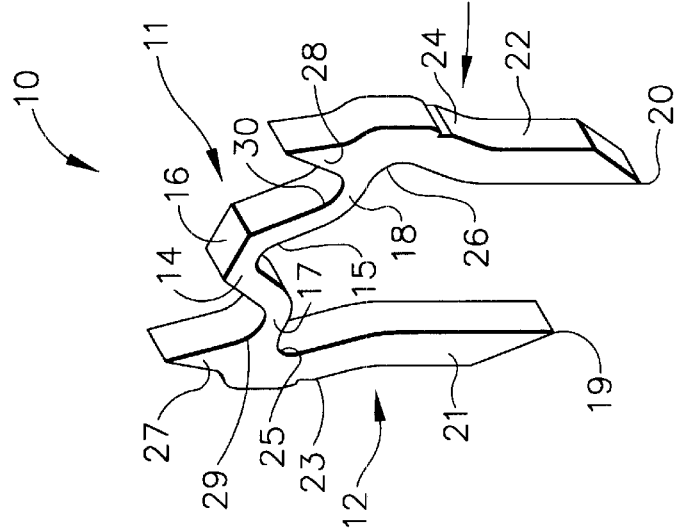
FIG. 1 is an isometric view of the implantable marker constructed in accordance with a preferred embodiment of this invention.
Figure 7:
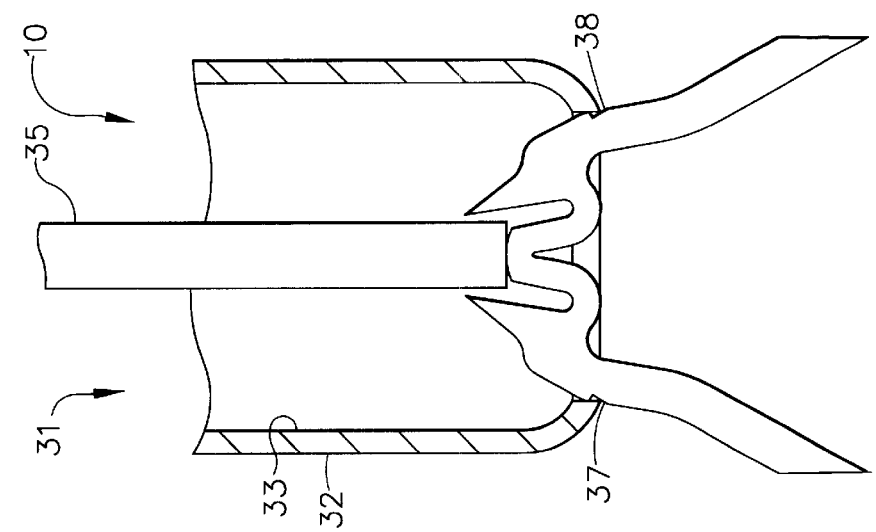
Figure 8:
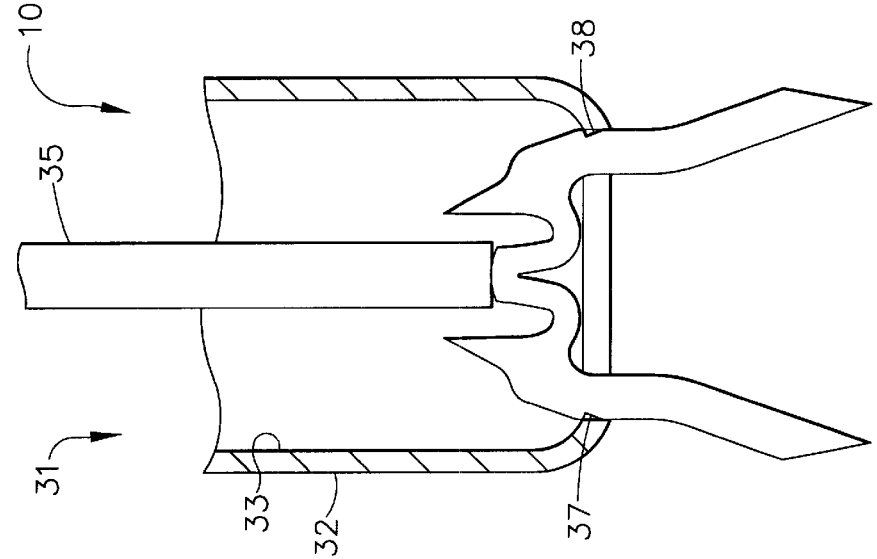

Referring initially to FIGS. 1–3, the preferred marker 10 of this invention is illustrated. The marker has a base 11 and first and second legs, 12 and 13, respectively. The base has an elevated bridge 14. The elevated bridge has an arcuate bottom surface 15. It also has a generally flat top 16.

The marker has a first transition 17 on one side of the elevated bridge and a second transition 18 on the other side of the elevated bridge. The first and second transitions separate the elevated bridge of the base from the descending first and second legs of the marker. The first leg has a first, beveled pointed tip 19 at the distal end of the leg remote from the first transition 17. Similarly, the second leg has a second, beveled pointed tip 20 at its distal end. Adjacent the first and second pointed tips of the legs, there are first and second straight leg arms, 21 and 22, respectively. Interposed between the first and second transitions and the first and second straight leg arms, are first and second camming marker surfaces 23 and 24, respectively. The camming marker surfaces extend outwardly from the straight leg arms of the legs. The first and second camming marker surfaces have first and second interior surfaces, 25 and 26, respectively, which are arcuate in configuration.

The marker has first and second reverse cleats, 27 and 28, respectively. The cleats are triangular in configuration. The first cleat protrudes from the first camming marker surface and the first transition. Similarly, the second cleat protrudes from the second camming marker surface and the second transition. The cleats protrude generally parallel to the first and second straight leg arms of the legs.

The marker has first and second camming marker surface notches, 37 and 38, respectively. The notches are generally V-shaped indentations in the camming surfaces. The first camming marker surface notch 37 is located on first camming marker surface 23 below first reverse cleat 27. Similarly, the second camming marker surface notch 38 is located on second camming marker surface 24 below second reverse cleat 28.

The bridge of the marker has a pair of top arcuate surfaces, 29 and 30, respectively, separated by the flat top of the bridge on the base of the marker. The first top arcuate surface 29 is bounded by the interior surface of the first spike and the surface adjacent the flat top of the elevated bridge. In a similar fashion, the second top arcuate surface 30 is bounded by the interior surface of the second spike and the surface adjacent the flat top.

The preferred marker is symmetrical about a centerline axis taken through the center of the elevated bridge 14 of the base of the marker, and drawn parallel to the first and second straight leg arms, 21 and 22, of the legs. The centerline axis is designated as "L" in FIG. 2. In addition, the region of the marker between the flat top of the elevated bridge and the arcuate bottom surface of the bridge can be characterized as a bridge flexure region of reduced thickness. The flexure region of the elevated bridge increases the flexibility of the marker when it is deployed from its pre-formed position to its open formed position. This increased flexibility, coupled with the arcuate symmetrical nature of the elevated bridge, provides a uniform load on the base of the marker during marker formation. In its pre-formed configuration, the first and second straight leg arms of the legs of the marker are generally parallel to each other.

The first and second reverse cleats of the marker are provided to prevent undesired migration of the formed marker when it is in its final open form configuration in tissue by preventing tissue from sliding off of the bridge. Consequently, the surface of the bridge firmly bears against tissue to prevent undesired migration of the marker.

Referring now to FIGS. 4–9, there is illustrated the deployment of the preferred marker of this invention from its pre-form configuration to its open form configuration. A marker applier 31 is provided which has a tubular shaft 32. The marker 10 is positioned inside the tubular shaft. The tubular shaft is sized so that the camming marker surfaces 23 and 24 of the legs of the marker contact the shaft inner wall 33 of the tubular shaft. The distal end of the tubular shaft has a distal camming wall surface 34 extending radially inwardly from the shaft inner-wall. The distal camming wall surface is sized so that this surface contacts the first and second straight leg arms of the legs of the marker when the marker is in its pre-form configuration, and the leg arms are parallel to each other as illustrated in FIG. 4. An applier push rod 35 is positioned on the flat top of the elevated bridge on the base of the marker, and the pointed distal tips of the legs protrude from the tubular shaft of the applier.

Figure 9:
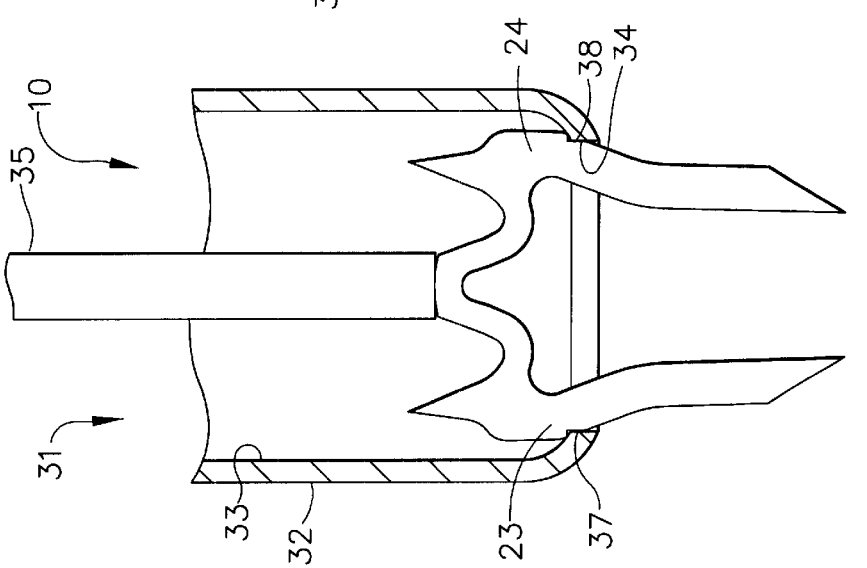

When the applier push rod 35 is pushed distally to deploy the marker from its pre-form position where the straight leg arms are parallel to each other to its open form position, the marker is urged out of the tubular shaft of the applier. As the marker moves distally within the tubular shaft of the applier, the camming marker surfaces of the legs of the marker are cammed against the distal camming wall surface of the applier. This camming action urges the straight leg arms of the legs of the marker to converge towards each other as the elevated bridge of the base of the marker bends inwardly at the bridge flexure region. As the camming marker surfaces of the legs slide against the distal camming wall surface of the applier, the distal camming wall surface of the applier eventually contacts the camming marker notch in each leg. At this point the convergence of the straight leg arms ceases and the straight leg arms begin to diverge as they pivot about the camming marker surface notch. They continue to pivot and diverge until the camming marker surface notch is forced past the distal camming wall surface of the applier. The applier push rod continues to apply force to the elevated bridge of the marker until the marker exits the distal end of the applier. The marker has formed a generally "W" shaped configuration as depicted in FIG. 9

The preferred applier for delivering and deploying the marker of this invention is described in detail in commonly assigned, copending application Ser. No. 09/105,570, filed Jun. 26, 1998

The marker of this invention can be made of any implantable material which is biocompatible and can exhibit the requisite motion and force to prevent inadvertent dislodgment of the marker when it is anchored in tissue. The preferred marker of this invention is composed of 316 LVM stainless steel (316 L stainless steel fabricated in a vacuum melt furnace for higher purity). Alternatively, the marker may be composed of absorbable polymers, as well as non-magnetic materials particularly suited for MRI imaging applications.

The marker can be advantageously mass produced using a conventional photoetching process to create a plurality of markers affixed to the desired carriers, typically a sheet of metal composed of 316 LVM stainless steel. The metal sheet can be cut into carrier rows, and sequentially fed into a cutting die for shearing the individual markers from the carrier rows.

The marker of this invention can be coated with agents to lower friction, stop bleeding or accomplish any other desired effect. Additionally the legs of the marker can be modified to include the addition of barb-like features that could increase the holding strength, migration resistance and imaging ability of the marker.

Although this invention has been described in connection with its most preferred embodiment, additional embodiments are within the scope and spirit of the claimed invention. The preferred marker of this invention is intended merely to illustrate the invention, and not limit the scope of the invention as it is defined in the claims which follow.

What is claimed is:

1. An implantable marker for implantation in tissue of a surgical patient, said marker comprising:
   a) a base, said base including an elevated bridge having a top and a pair of top arcuate surfaces separated by said top, said bridge bounded by first and second transitions;
   b) a first leg descending from said first transition of said base, said first leg including:
      i) a first distal tip remote from said first transition;
      ii) a generally straight first leg arm adjacent said first distal tip; and
      iii) a first camming marker surface between said first transition of said base and said first straight leg arm, said first camming marker surface extending outwardly from said first straight leg arm;
   c) a second leg descending from said second transition of said base, said second leg including:
      i) a second distal tip remote from said second transition;
      ii) a generally straight second leg arm adjacent said second distal tip; and
      iii) a second camming marker surface between said second transition of said base and said second straight leg arm, said second camming marker surface extending outwardly from said second straight leg arm;

d) a first camming marker surface notch located on said first camming marker surface, and a second camming marker surface notch located on said second camming marker surface;

wherein said first and second straight leg arms are generally parallel to each other when said marker is in a pre-formed configuration, and said first and second straight leg arms initially converge towards each other from a spaced-apart position adjacent said first and second transitions and then diverge into an open form configuration so that the distal tips of said legs are separated from each other.

2. The implantable marker of claim 1 wherein said marker is symmetrical about a centerline axis drawn parallel to said first and second straight leg arms and taken through the center of said elevated bridge of said base of said marker.

3. The implantable marker of claim 2 wherein said marker has a "W"-shaped configuration in the open form configuration.

4. The implantable marker of claim 3 wherein said first and second distal tips of said legs are beveled pointed tips.

5. The implantable marker of claim 4 wherein said elevated bridge has an arcuate bottom surface.

6. The implantable marker of claim 5 wherein said elevated bridge has a generally flat top, and said bridge includes a bridge flexure region of reduced thickness between said flat top and said arcuate bottom surface of said elevated bridge.

7. The implantable marker of claim 1 further comprising a first reverse cleat protruding from said first camming marker surface and said first transition, and a second reverse cleat protruding from said second camming marker surface and said second transition.

8. The implantable marker of claim 7 wherein said first and second reverse cleats are generally triangular in configuration.

9. The implantable marker of claim 8 wherein said first and second reverse cleats protrude generally parallel to said first and second straight leg arms of said legs.

* * * * *